United States Patent [19]
Studor et al.

[11] Patent Number: 6,152,856
[45] Date of Patent: Nov. 28, 2000

[54] REAL TIME SIMULATION USING POSITION SENSING

[75] Inventors: George F. Studor, Houston, Tex.;
Robert W. Womack, Missoula, Mont.;
Michael F. Hilferty, Florence, Mont.;
William B. Isbell, Missoula, Mont.;
Jason A. Taylor, Bozeman, Mont.;
Bruce R. Bacon, Forest Grove, Oreg.

[73] Assignee: Real Vision Corporation, Seattle, Wash.

[21] Appl. No.: 09/077,242

[22] PCT Filed: May 8, 1997

[86] PCT No.: PCT/US97/07721

§ 371 Date: May 22, 1998

§ 102(e) Date: May 22, 1998

[87] PCT Pub. No.: WO97/41925

PCT Pub. Date: Nov. 13, 1997

Related U.S. Application Data

[60] Provisional application No. 60/017,417, May 8, 1996.

[51] Int. Cl.[7] .................................................. A63B 21/00
[52] U.S. Cl. .................................... 482/8; 482/4; 482/57; 482/902; 434/247
[58] Field of Search ................................ 482/1–9, 51, 52, 482/54, 57, 900–902; 434/247

[56] References Cited

U.S. PATENT DOCUMENTS

| | | | |
|---|---|---|---|
| 5,466,200 | 11/1995 | Ulrich et al. | |
| 5,547,439 | 8/1996 | Rawls et al. | |
| 5,591,104 | 1/1997 | Andrus et al. | |
| 5,890,995 | 4/1999 | Bobick et al. | 482/4 |
| 5,947,868 | 9/1999 | Dugan | 482/4 |

*Primary Examiner*—Glenn E. Richman
*Attorney, Agent, or Firm*—Dorsey & Whitney LLP

[57] ABSTRACT

An interactive exercise system including exercise equipment having a resistance system, a speed sensor, a controller that varies the resistance setting of the exercise equipment, and a playback device for playing pre-recorded video and audio. The controller, operating in conjunction with speed information from the speed sensor and terrain information from media table files, dynamically varies the resistance setting of the exercise equipment in order to simulate varying degrees of difficulty while the playback device concurrently plays back the video and audio to create the simulation that the user is exercising in a natural setting such as a real-world exercise course.

23 Claims, 6 Drawing Sheets

REAL TIME SIMULATION USING POSITION SENSING

CROSS-REFERENCE TO RELATED APPLICATIONS

This application claims the benefit of U.S. Provisional Application No. 60/017,417 filed May 8, 1996.

RIGHTS IN OTHERS

The present invention was not made under government contract, but one of the inventors was at the time of invention an employee of the National Aeronautics and Space Administration (NASA). Pursuant to Title 37 Code of Federal Regulations part 501, NASA has indicated that title will be left in the individual inventors, subject to reservation by the United States Government of a nonexclusive license for governmental purposes.

TECHNICAL FIELD

The present invention relates generally to exercise equipment, and more particularly to a system to simulate real world exercise courses to users operating such exercise equipment.

BACKGROUND ART

Exercise is necessary. Medical studies have related important health problems to the lack of it, and it clearly affects our moods, our sense of self-image, and the public image by which others perceive us. However, increasingly people are not getting the amounts or the types of exercise which they need. Many reasons exist for this, but some particular ones are boredom, self consciousness, the difficulty or inability to go somewhere to exercise, and even complex social pressures.

Exercise is considered boring, and repetitive exercise is considered particularly so. A major reason for this is that exercise today frequently is not practical in natural or varied settings. For example, to run in many urban settings there may be little choice but to use an inside track or even a treadmill at a health club or gym, and to use that same facility day after day.

When people do want to exercise, finding a suitable place to do so can be difficult. A health club, gym, or park may not be near by, or may be too crowded with others also seeking exercise or even unrelated use of the facility. And for some, exercise is particularly difficult due to physical handicaps which limit their ability to travel anywhere. This is particularly unfortunate, because it is handicapped people who often have greater needs for exercise than most, due to impaired mobility or due to the need for physical rehabilitation.

Somewhat related to the where-to-exercise issue is time efficiency of exercise. Travel to public indoor exercise facilities takes time, and upon arrival there may then be a wait to use the exercise resources of preference. As our society increasingly turns to working at home (particularly as new telecommuting capabilities so permit), the time inefficiency of traveling to exercise becomes even more apparent.

Exercising in traditionally public settings such as health clubs and gyms can also be awkward feeling or even embarrassing to many. Some people are simply shy, and do not want to exercise where they are constantly reminded that they are surrounded by others. Others are self conscious about their own physical condition, particularly in a "comparative" setting like a health club, and they are therefore uncomfortable exercising in public (unfortunately such people may need exercise the most, for instance because they are overweight).

Even factors in our diverse society tend to suppress exercise in some ways. For example, the genders and ages tend to separate quite distinctly in regard to what equipment they use at health clubs, what gyms they patronize, and even what sections of parks they use. Further, regrettably, this is not always the exercising individual's own choice.

In sum, there are many complicated reasons why we do not exercise. Some of these may never be entirely overcome. However, furthering exercise to the extent possible is a worthy goal, and governments have long recognized the physical condition of the populace as a national priority. For an example, the existence and the importance of the National Counsel on Fitness in the United States.

Today, many see perception of the exercise environment as a key to increasing the participation in, the enjoyment of, and ultimately the success of exercise. Thus, efforts are being made to change the exercise environment, with some of the rationale being; if one cannot exercise in a natural manner, then use an exercise machine to work the same muscles in the same manner; if one cannot go to a natural setting, then create the illusion of one; if one cannot go to where exercise equipment is (e.g., a health club or gym), then bring exercise equipment to the user; if one does not want their gender or age to be a factor in the social dynamics of group exercise, then hide such by distracting the other users of such, or even camouflaging oneself in some manner.

The current situation, and the focus on the exercise environment, have created large and growing specialty segments in the exercise equipment market. Home exercise equipment is one such segment. But regrettably, it is one which is not very successful at delivering what its consumers want, because those who do exercise at home typically do not find that they enjoy or can stick with exercise there for very long. One reason for this is that the home setting is often even more boring than other settings, and another is that the home is often full of distractions.

"Virtual Reality" exercise equipment is another such market segment (one which has potential overlap with the home market, but which has largely failed to do so to date). Several major manufacturers of exercise equipment (e.g., Tectrix, Nautilus, Life Fitness, Transcape, Kettler, Precor, and Reebok) have developed such exercise machines. These machines overwhelmingly rely on animated computer graphics which use a high degree of user interactivity. However, since it is generally perceived that development costs of animated computer environments are prohibitive, consumer price resistance is generally anticipated by manufacturers, and accordingly their product offerings are fewer. For such machines that are developed and marketed, the price then often limits sales to organizations such as health clubs, rehabilitation centers, and special government installations, and when such equipment is available, even at these locations, it often cannot be used by all who might wish to do so.

The present invention acknowledges that exercise environment is the key. However, the term "virtual reality" is not entirely appropriate, and the approach disclosed herein may more appropriately be termed "natural environment simulation."

DISCLOSURE OF INVENTION

Accordingly, it is an object of the present invention to provide an exercise system which dynamically simulates exercise in a natural environment.

Another object of the invention is to provide an exercise system which realistically simulates exercise in a natural environment.

And, another object of the invention is to provide an exercise system which is economical and which uses equipment and methods that are conventional enough that relatively unsophisticated users may employ the system for exercise in public facilities as well as private settings.

Briefly, one preferred embodiment of the present invention is an interactive exercise system including an exercise machine having resistance setting capability and speed sensing capability. Also included is a controller suitable for adjusting resistance of the exercise machine, for collecting speed data from it, and for communicating bidirectionally with a computer system. The computer system reads media containing previously recorded course data, and based upon the speed data from the exercise machine and the pre-stored course data, calculates and appropriately directs the controller to dynamically control the resistance of the exercise machine so that varying degrees of difficulty are simulated as a user operates the exercise machine, as would be consistent with what would be experience traveling through a real exercise course.

An advantage of the present invention is that very dynamic exercise may be carried out with it, yet without undue user involvement in setting effort levels for the exercise. A user may, optionally, initially set a nominal difficulty level, and then let the inventive exercise system dynamically control the difficulty thereafter, to present that varying effect of exercising in the changing terrain of a real world exercise course.

Another advantage of the invention is that it realistically simulates a real world exercise experience. True nature video content is used, which is captured in natural settings along real world courses, rather than computer animations and graphics, or such superimposed upon nature still scenes. The user may optionally select that natural sound content be added to the experience, or may opt for verbal feedback and encouragement, or for music to set a mood or to entertain.

And, another advantage of the invention is that it is economical to implement and operate. It may employ relatively conventional exercise equipment having resistance setting and user speed collecting capabilities. It may also employ a conventional computer system using relatively standard audio and video hardware, and using widely used and well understood operating system software. The media used by the invention to store audio, video, terrain information, and optional other files may be any of many widely available and inexpensive formats, and accordingly media units containing exercise sessions can be quickly and relatively cheaply produced, reproduced, and distributed to the ultimate users of the invention.

These and other objects and advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

The purposes and advantages of the present invention will be apparent from the following detailed description in conjunction with the appended drawings in which.

BEST MODE FOR CARRYING OUT THE INVENTION

Figure 1:
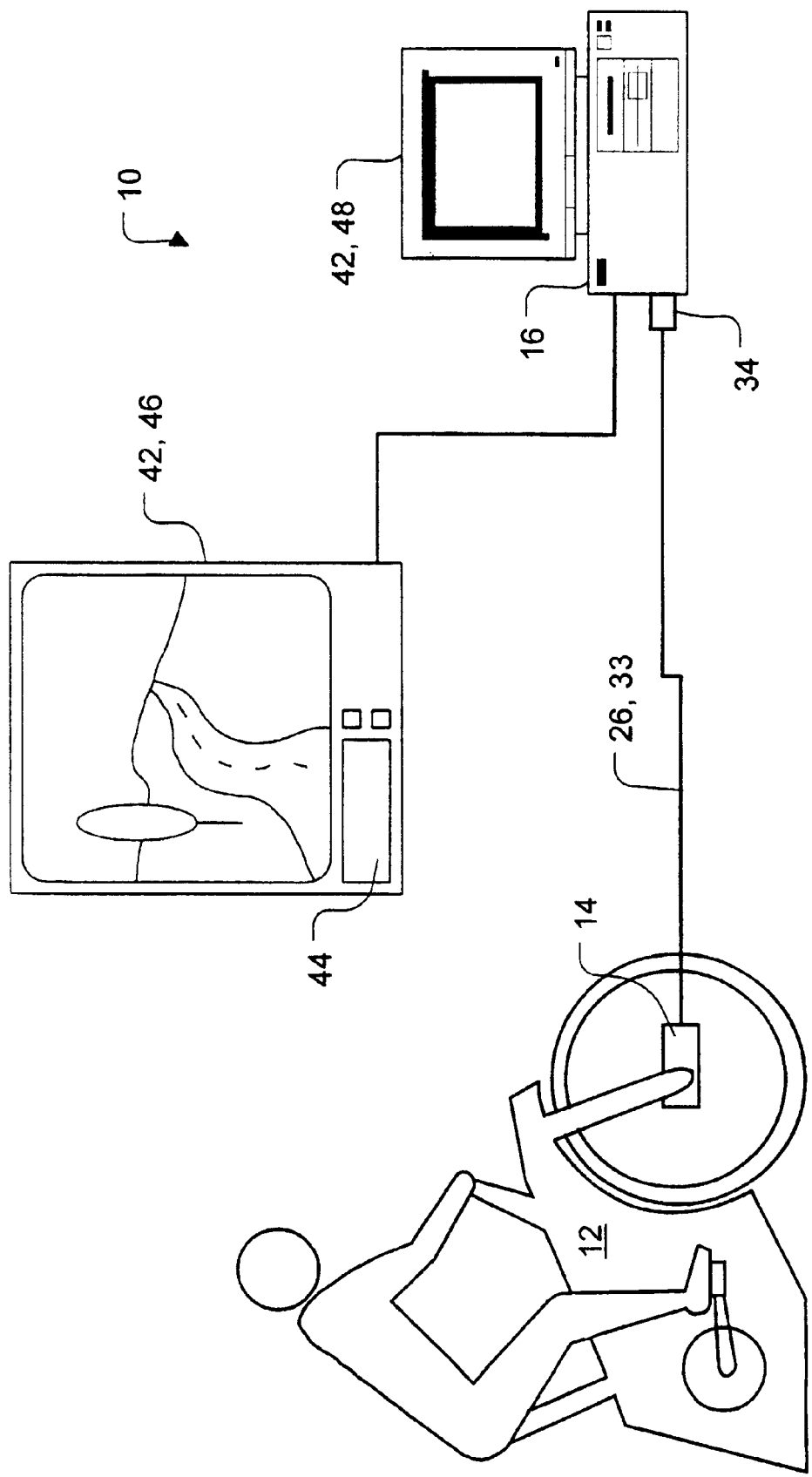
FIG. 1 is a depiction of a user applying the present inventive exercise system.

A preferred embodiment of the present invention is an interactive exercise system employing simulation of real-world exercise courses. As illustrated in the various drawings herein, and particularly in the view of FIG. 1, a form of this preferred embodiment of the inventive system is depicted by the general reference character 10.

As depicted in FIG. 1, the exercise system 10 may be viewed as including the following major components: exercise equipment 12, which is suitably featured or modified; a M-S converter 14, which acquires data from and controls some aspects of the operation of the exercise equipment 12; and a computer system 16, which uses a software program 18 and pre-recorded media 20, to operate the exercise system 10 and present to the user the simulation of a real-world exercise experience.

Figure 2:
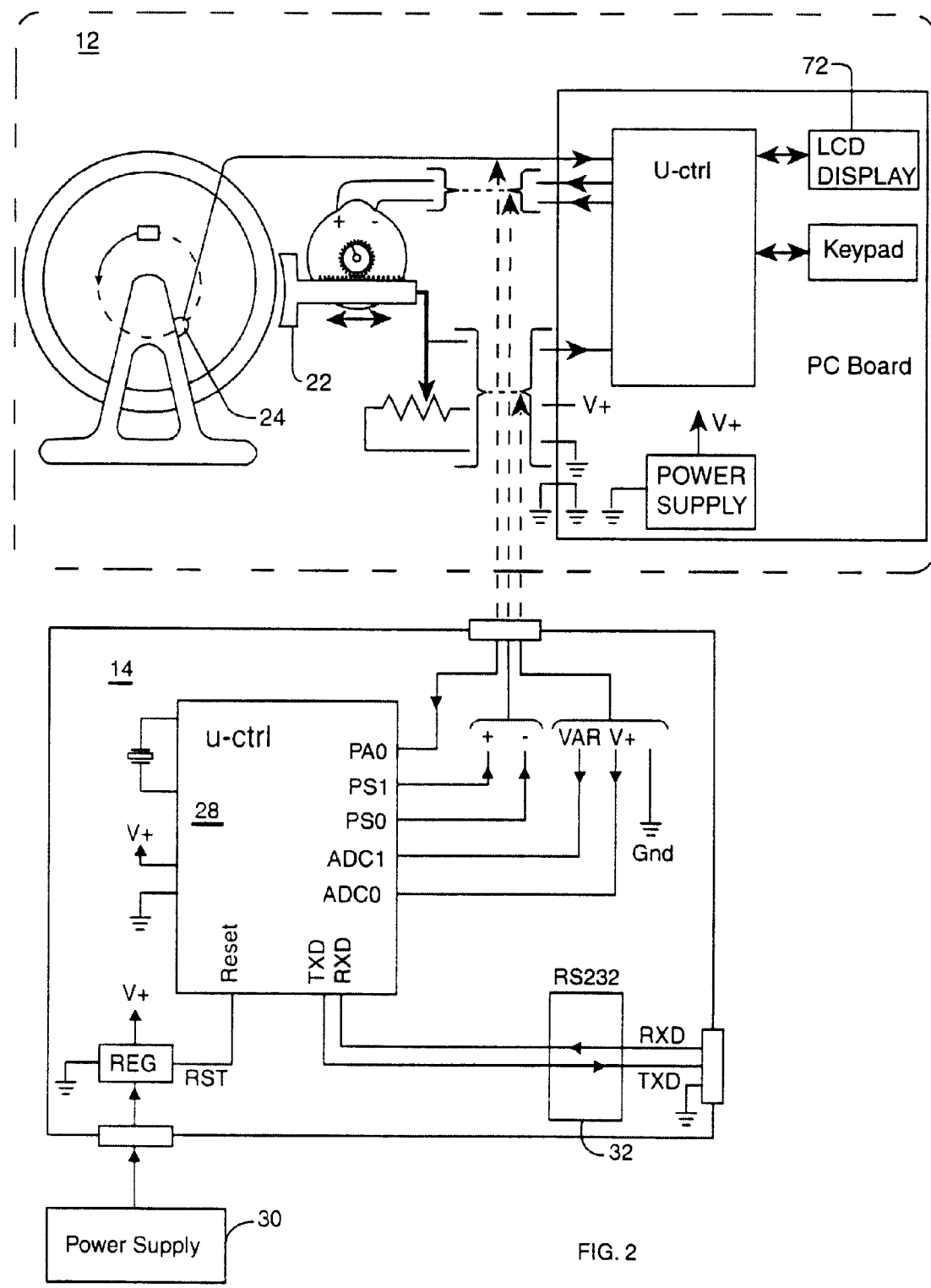
FIG. 2 is a stylized block diagram of the M-S converter component of the invention, one suitable for use with a typical existing exercise device.

The exercise equipment 12 allows the user to interact directly during exercise with the simulated environment created by the other components of the exercise system 10. The nature of the specific exercise equipment 12 which is used can vary considerably. FIG. 1 depicts an exercise bicycle being used, but treadmills, stairsteppers, rowing machines, ski machines, and other equipment are equally suitable. The exercise equipment 12 includes, as a minimum, an adjustable resistance system 22 and a speed sensor 24 (FIG. 2). The user may set a nominal difficulty level for exercise by adjusting the resistance system 22, then, as the exercise equipment 12 is operated, the speed sensor 24 provides data from which the user's actual efforts can be inferred.

Various exercise equipment 12 on the market today comes with any of several suitable configurations of both speed sensors 24 and resistance systems 22. Alternately, such may easily be retro-fitted to many types of existing exercise equipment 12. Some commonly available speed sensors 24 include reluctor, hall-effect, tachometer, and pulse creating alternator type devises. Some commonly used resistance systems 22 are friction and magnetic braking devices (e.g., electronically adjustable brakes using a motor or electro-magnet system, and even brakes powered from an alternator used in the speed sensor 24). These are typically controlled by motor-driven actuators, and many are able to provide feedback indicating the current brake setting.

FIG. 2 illustrates in schematic block diagram format an embodiment of the M-S converter 14, and its connection with suitable exercise equipment 12. The term "M-S converter" is used by the inventors because it is representative of the motor-brake type resistance system 22 and the magnet with magnetic pick-up type speed sensor 24 which are used in their preferred embodiment. The M-S converter 14 performs two major tasks. One is to receive commands from the computer system 16 to control the resistance system 22 of the exercise equipment 12, and the other is to acquire data from the speed sensor 24 of the exercise equipment 12, to convert that data as needed, and to then transmit it through a communications link 26 to the computer system 16. The M-S converter 14 may be either integrated into the exercise equipment 12 by the original equipment manufacturer (OEM), or it may also be retro-fitted to existing exercise equipment 12.

The M-S converter 14 includes circuitry to drive commonly used resistance systems 22, and to receive information from commonly used speed sensors 24 (some examples of both have been noted above). The M-S converter 14 also includes circuitry to perform signal-conditioning and to communicate with the computer system 16, via the communications link 26. In the preferred embodiment (see e.g., FIG. 2), the M-S converter 14 includes a micro controller 28 (e.g., a Motorola® MC68HC11) with integrated analog-to-digital capability, internal data communication capability, and sufficient memory for its role. A suitable external power supply 30 is chosen to meet the demands from the hardware of the M-S converter 14, as is circuitry to condition the signals coming from and going to the exercise equipment 12. A RS-232 Receiver/Transmitter integrated circuit (IC) communications port 32 interfaces the micro controller 28 to the communications link 26, and in turn to the computer system 16.

The communications link 26 is bi-directional for communications between the computer system 16 and the M-S converter 14. In the preferred embodiment, the communications link 26 utilizes a cable 33 which is suitably terminated with appropriate connectors at both of its ends to connect to the M-S converter 14 and the computer system 16. When using a cable type system, a desirable but optional component is an interconnect adapter 34. Robust activities are typical in environments around exercise equipment, and this frequently leads to the need to replace damaged cables 33. Mindful of this, the inventors in their preferred embodiment use cables 33 which may be rapidly and economically procured and installed by relatively unsophisticated personnel. For example, the M-S converter 14 may be constructed with a socket for an RJ12 connector, and an interconnect adapter 34 may be used at the computer system 16 end which converts from RJ12 to DB9 (or RJ12-DB25 on computers using the older DB25 standard; an RJ45 connector could also be used). It is thus possible to use conventional telephone cables with RJ12 or RJ45 ends as the vulnerable cable 33 component in the communications link 26. Such telephone cables are very widely available and inexpensive, and they are polarized and genderized at their ends in manners such that confusion as to their connection is virtually impossible (notably unlike the plethora of cables available for conventional computer ports).

Of course, it also is possible for the communications link 26 to transfer data via other means. For example, rather than use the presently preferred serial data transfer protocol, an embodiment could easily be constructed to use a computer parallel port, although such would necessarily have restricted length of the cable 33, due to the electrical limitations of such ports (3–5 meters, vs. 75 meters or greater for standard serial protocols). Alternately, infra-red (IR; e.g., IrDA protocol) or radio frequency (RF) transmission can be used in the communications link 26, and the cable 33 then dispensed with entirely.

Figure 3:
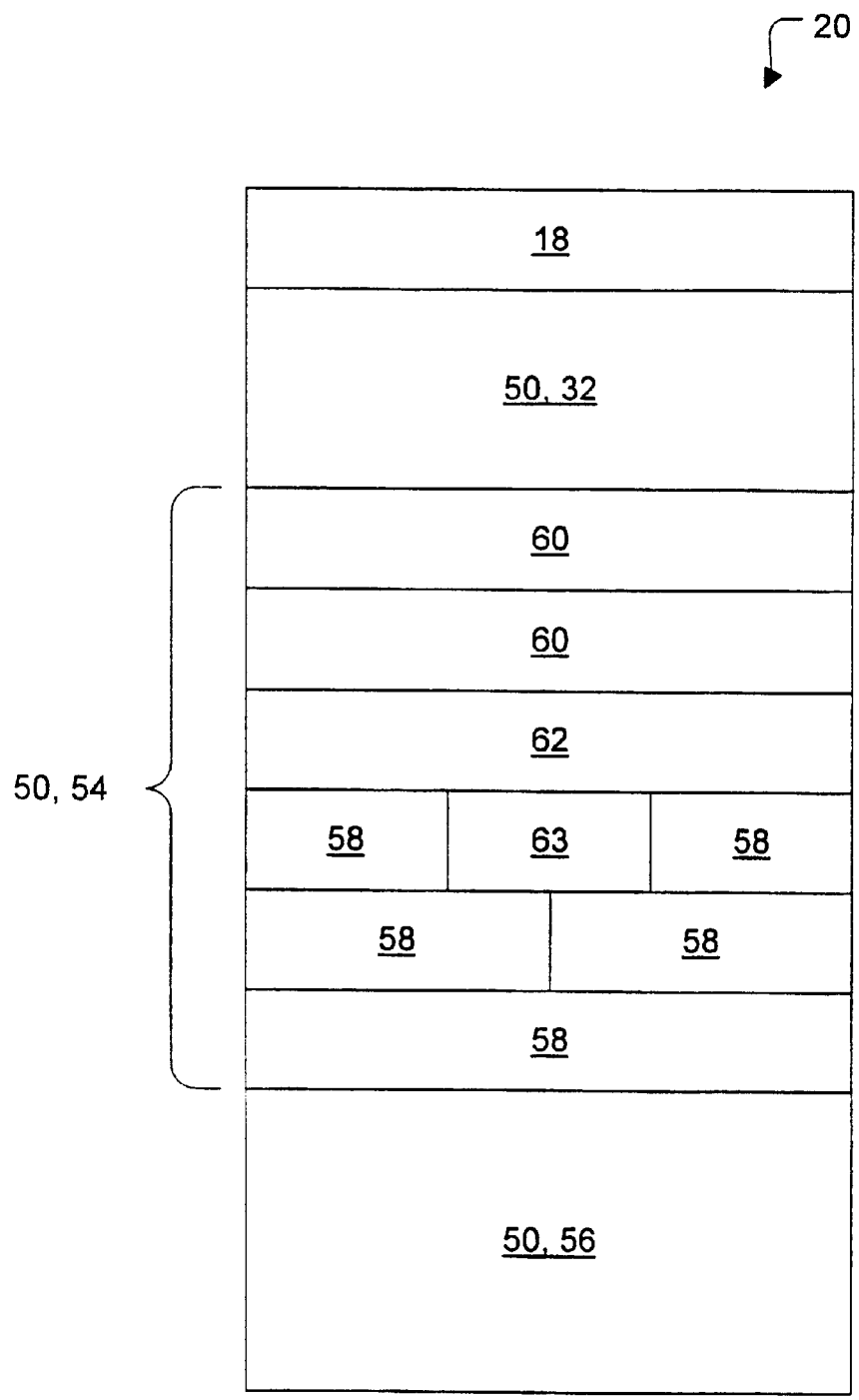
FIG. 3 is a block diagram which is representational of files stored on pre-recorded media which the exercise system may use.
Figure 4:
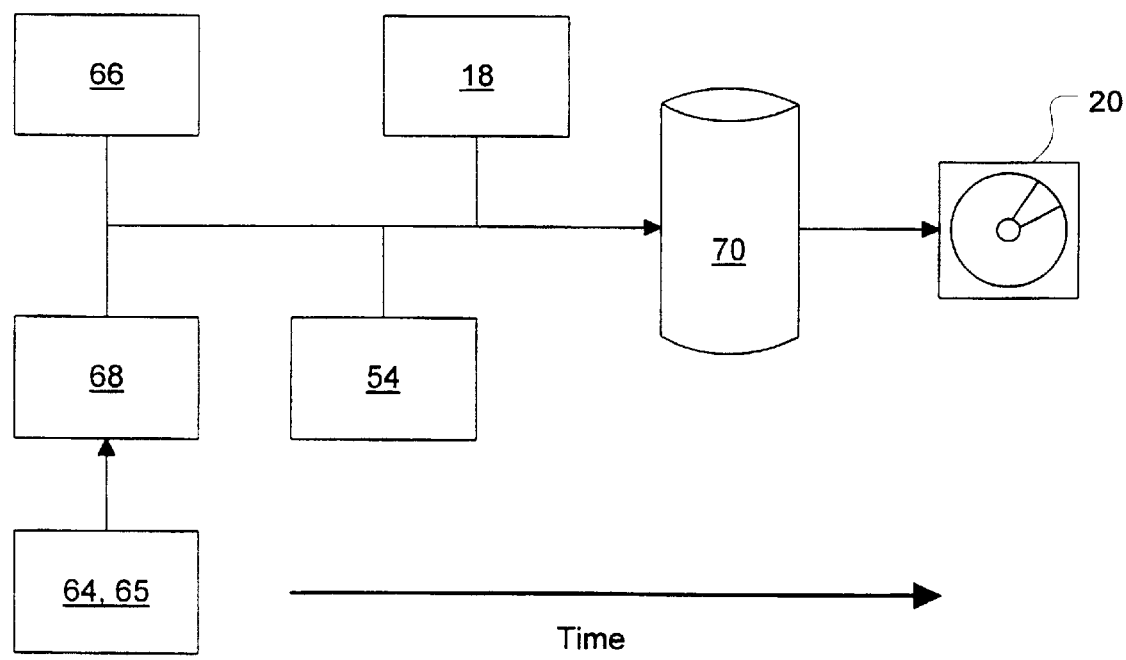
FIG. 4 is a block diagram depicting sources and a timeline for collection of data used to record the media.

Returning to FIG. 1, the computer system 16 provides a user interface, operating platform, and processing for the software program 18 (FIGS. 3 and 4). It affords users interactivity to control audio-video environments assembled and played from the data contained on the media 20, and it may provide difficulty feedback and other status information to the user (if such is not provided by a display system at the exercise equipment 12, or the computer system 16 may even provide redundant difficulty feedback). The computer system 16 may be a suitably featured personal computer (PC), or other platform, which includes a media player 36, an audio sub-system 38, a video sub-system 40, and a monitor 42. For their initial embodiments, the inventors have used a computer system 16 which includes a Pentium 100 Mhz central processing unit (CPU; Pentium is a T/M of Intel Corporation, of Santa Clara, Calif.), a peripheral component interconnect (PCI) bus, and 16 megabytes of fast page mode or extended data output (EDO) type dynamic random access memory (DRAM). Of course, other hardware may be substituted. For example, the PowerPC processor (PowerPC is a T/M of Motorola Inc. of Shoumberg, Ill.) appears to satisfy known requirements for the exercise system 10.

To facilitate ease of use of the exercise system 10 for setting-up exercise sessions, for interactively controlling them, and for later summarizing and comparing session statistics, existing user familiarity with conventional computer graphical user interfaces (GUI) may be used to great advantage (and for users lacking such experience, there is a wide range of training resources for such GUI). For example, the computer system 16 may use typical GUI type operating systems such as Windows95 or WindowsNT (both T/M of Microsoft Corporation of Redmond, Wash.), or Macintosh System7 (T/M Apple Computers, Inc. of Cupertino, Calif.), or the Next operating system (T/M of Next Computer Corporation, of Menlo Park, Calif.). Further, in addition to their ease of use and the existing large base of already trained users, such GUI particularly lend themselves to real-time display and recording of exercise data (e.g., speed, heart rate, terrain profile maps, multiple exercise session comparisons, etc.). Such GUI and appropriate options in the software program 18 can thus allow users the flexibility to select what they want to display if anything. And, data acquisition of exercise data with third party evaluation programs, exercise journal software, internet/modem racing, and other features may be provided in enhanced embodiments of the exercise system 10.

The media player 36 may be of any type suitable for the particular media 20 employed (described below). It is anticipated that in many embodiments the media player 36 will be mounted in the computer system 16 itself, but an external device may also be used (one very "external," if the computer system 16 includes a network computer or network terminal, also discussed below). The present preferred embodiment uses CD-ROM type media 20, and accordingly the media player 36 used in the preferred embodiment may be a CD-ROM drive or a DVD drive (Universal Disk Format, also sometimes termed Digital Versatile Disk, a new high capacity format just now entering the market; the disk players for DVD can also read CD-ROM disks). As higher capacity media 20 become more widely available, higher quality video and longer workouts with more room for novel value added components may be incorporated into the media 20. Some examples include interactive coaching and multiple music tracks to chose from; say classical, rock, jazz, rap, vocal, environmental nature sounds, etc.

The audio sub-system 38 of the computer system 16 reproduces the audio data stored in the media 20. For this the computer system 16 includes a suitable "sound board" ("board" is an industry convention which will be used herein, but is somewhat a misnomer since many computers now have such capabilities integrated into the motherboard; note that a separate such "board" is not shown, since most will be located inside the computer system 16). To convert electrical signals into sounds which users can hear, the audio sub-system 38 also includes at least one speaker 44 (or headphones). FIG. 1 depicts a speaker 44 included in a television 46 (one type of possible monitor 42).

The video sub-system 40 reproduces video data stored in the media 20, and outputs either or both of television (TV) type video or SVGA signals to the monitor 42 used by the exercise system 10. Users view the playback of video data on a monitor 42 (e.g., color television 46, TV goggles (not shown), or a computer monitor 48) which has suitable resolution and refresh rate to provide crisp viewing of video presentation.

Virtually all computers today already include some type of "video board" (i.e., video signal creation capability) and a computer monitor 48. Where these are suitably powerful, they may be used by the video sub-system 40, although there will then be a need to switch modes of viewing between control and video playback for set-up and use of the exercise system 10. To avoid this, and to obtain higher video performance, a separate video sub-system 40 may be incorporated into the computer system 16, for dedicated use by the exercise system 10. FIG. 1 depicts such an embodiment, one where a television 46 (including a speaker 44 for use by the audio sub-system 38, as noted above) is "driven" by an auxiliary video board (not shown since it is typically contained within the computer system 16). In this embodiment the primary video board of the computer system 16 drives the computer monitor 48 and the auxiliary video board of the computer system 16 drives the external television 46. This also provides the advantage that the television 46 may be placed close to the user, and the computer system 16 with its own dedicated computer monitor 48, may be placed wherever convenient.

For very high performance embodiments the video sub-system 40 may even be specially optimized with a proprietary video board to provide high resolution and smooth varying speed in the display of video data to the user. To implement such a proprietary video board the inventors have used to advantage a particular feature of many modern computer components, programmable BIOS stored in flash ROM. Today many sophisticated electronic devices, including video boards, use micro processors executing pre-stored programs widely referred to as BIOS (Basic Input and Output System). Today such BIOS is increasingly stored in flash ROM integrated circuits, ostensibly for end users to later be able to upgrade the BIOS as "bug fixes" and improvements are developed by the original device manufacturers. Flash ROM is erasable and re-programmable multiple times by those having suitable knowledge to do so (ROM: Read Only Memory, is admittedly a misnomer in the context of flash ROM, but a term the electronic industry still uses). For some embodiments, the inventors thus reprogram the flash ROM of suitable existing video boards to create particularly efficient embodiments for the exercise system 10.

It should be noted, however, that a proprietary video board is not a necessary component in the present video sub-system 40. Many presently available video boards provide adequate levels of performance. Which is good, since there will always be some who are unwilling to pay for customized video capability, or who are unwilling to install and use such (e.g., due to lack of technical sophistication or confidence to self install and configure an option in a computer). Further, video board capabilities are constantly being improved, so that default manufacturer provided capabilities may soon surpass those desirable for the exercise system 10. But alternately, the view can be taken that available default video capabilities, particularly in regard to resolution and speed, will always be somewhat less than the continually increasing expectations of users. Accordingly, it should be appreciated that the present invention is able to employ either standard or specially tailored video capability for particular situations.

Regardless of what type of video board is employed, the media 20 may optionally include the newest versions of suitable video drivers. In this manner, when the media 20 is loaded onto the computer system 16 the drivers may be checked for currentness (e.g., with a Windows95 auto-run procedure), and if appropriate the users with little or no computer experience can update the drivers by being guided through the update process.

Emerging technology is continually remolding the definition of what is a computer system, and the present exercise system 10 is quite able to employ such evolving technology to advantage. It should particularly be noted that not all components of the computer system 16 need to be physically present in one "box," or even at one location. Computer networking, and particularly the Internet, are today broadening computer capabilities considerably. The exercise system 10 may also use such technology. For example, users located on different continents may employ the exercise system 10 with Internet connected network computers (NC) and media 20 on a server computer, perhaps actually located on yet another continent, to hold "communal" exercise sessions in concert, for competitive sporting events, or for coached exercise regimes.

Alternately, the exercise system 10 may use one powerful computer system 16 to run exercise sessions for multiple users on multiple instances of exercise equipment 12. These sessions may be quite different, using entirely different data from the media 20, or they may be for exercise in concert or in competition. For example, a health club might employ the exercise system 10 with one computer system 16 to concurrently control a variety of exercise equipment 12 for its various individual member-users, all in manners suiting their individual tastes and capabilities.

In the preferred embodiment, the inventors presently store information for one complete course on a CD unit of media 20 (e.g., typically one 45-minute session, which may be repeated, or which may even be broken into shorter sessions and then presented in varying sequence). However, as higher capacity media 20 become available, longer courses and even multiple unrelated courses may be stored on one physical storage unit. It should, however, be appreciated that storage media other than a CD (compact disc) may also be used. For example laser-disks would be quite suitable. Further, as increased capacity storage media becomes available they may also be suitable (e.g., DVD media, now becoming available). Alternately, the media 20 may be stored in a suitable mass storage system, say on a very high capacity hard drive on a network server within the computer system 16.

The media 20 (FIG. 3) contains three general types of pre-recorded data files 50: video files 52 (e.g., compressed AVI or MOV formats), audio files 54 (e.g., in WAV, MIDI and other formats), and table files 56 of normalized terrain characteristic data (e.g., slope data), which associate terrain characteristics to particular times in a video file 52. The video files 52 are, in particular, different from those typically used by prior art systems. The present exercise system 10 does not use computer animations or graphics to present a visual substitute for the course, techniques which are notoriously labor intensive and therefore time consuming and expensive. Instead the exercise system 10 uses actual captured video of real-world courses. This fundamental distinction from most of the prior art makes exercise with the invention much more lifelike, and additionally makes it much cheaper to develop the media 20.

Multiple types of audio files 54 may be provided. Two of these, voice audio files 58 (e.g., currently popular Spinning workouts at health clubs could be done at home in the natural environment simulation provided by the exercise system 10, with a spinmaster giving workout commands) and music audio files 60 are used in generally conventional manners. However, two other types of audio files 54 may also be used by the invention which are not typically found in prior art systems. These are environmental audio files 62 (e.g., of animals such as birds, wind in the trees, and running water) and effects audio files 63 (e.g., sound effects such as bicycle gear shifts). Of course, the use of environmental sounds to enhance simulations of nature has long been known, but generally not in the context of a nature simulating exercise system. As noted prior art systems have relied primarily on computer animations, and sound content, where even provided, has generally had similar "cartoon" like qualities. Similarly, the use of sound effects has a long history (e.g., in computer games), but not in concert with other types of sound content and in the present manner.

The media 20 may also contain the software program 18, for loading into and execution on the computer system 16. However this is not a requirement. The software program 18 may be supplied entirely separately (e.g., downloaded from a bulletin board, BBS, or an Internet site). The executed version of the software program 18 may be stored in mass storage on the computer system 16, rather than it being loaded from the media 20 each time before use, thus permitting all of the capacity of a unit of the media 20 to be dedicated to the data files 50. Alternately, a version of the software program 18 may be included in some (not necessarily all) instances of the media 20, and if an existing version which is already loaded and executing on the computer system 16 detects that the version stored on the media 20 is newer (i.e., an upgrade, entirely or in part), the user may be prompted whether they want to install the new version from the media 20 into the computer system 16 for use thereafter. Further, as somewhat already discussed, still additional types of data may also be stored on the media 20 (e.g., video driver updates).

The media 20 used with the exercise system 10 are produced by acquiring position and terrain characteristics for real-world courses for the table files 56, by acquiring video data for the video files 52 which is representative of a human viewer's perspective as they would travel through the course, and by acquiring audio data for the audio files 54 (e.g., by dubbing in voice overs and music soundtracks or natural environment sounds to match the acquired terrain and video data), and by storing all of these along with synchronizing information in the media 20. This generalized approach of mapping normalized terrain characteristic data facilitates the creation of new video environments. The terrain characteristic data is simultaneously collected with the video data using a time interval which ensures that changes in terrain characteristic seems smooth and continuous to the user.

The terrain characteristic types used by the exercise system 10 can quite varied. When the inventors initially developed the exercise system 10, they appreciated that many real world courses had variations in slope, and accordingly this is one terrain characteristic which the invention is quite capable of simulating. However, other terrain characteristics may also be used. For example, for use with a rowing machine as the exercise equipment 12 the appropriate terrain characteristic data might be current and wind, to simulate the experience of rowing up a river or across a lake. Another example is simulation of variations in running surface, say from earthen path to sandy beach to asphalt running track.

Further, terrain characteristics which may not easily be simulated directly (e.g., altitude or temperature variation) may nonetheless be recorded in the data files 50, and the software program 18 may be used to control the exercise equipment 12 a suitable manner to apply a variable "handicap" (or more preferably termed, an "indirect feedback") which simulates the varying effort levels required of users on such a real world course. Indirect feedback can also be used to anticipate particular exercise scenarios, based upon exercise session characteristics up to a present point or even based on statistically gathered user information. For implementations of the software program 18 using such indirect feedback, fuzzy logic techniques may be beneficially employed. Accordingly, there is quite broad variety of terrain characteristics which are appropriate for recording in the media 20, and the true spirit of the present inventive exercise system 10 encompasses that variety.

To enhance the quality of the terrain data, it may be obtained by reference to accurate standards 64 (FIG. 4). The inventor's preferred embodiment uses reference to a Global Positioning Satellite system (GPS system 65). However, it should be appreciated that ground based radio frequency, optical, and other long used conventional systems can all be used for this standard 64. Similarly, electronic altimeters, odometer recorders, electronic or regular inclinometers, and even manually adding grade information based upon visual previews of courses are other examples of standards 64 which may be employed.

One method used by the inventors to concurrently collect slope terrain data and video data for cycling has been to record the known overall distance of a course; record the video in real-time using a firewire connection between the video camera and a PC logging the data; and varying travel speed in accordance with a normalized data set derived from empirical data collected from the speed of an actual cyclist in accordance with the slope terrain, i.e. 6 degree slope=8 MPH and a zero degree slope=20 MPH, etc. In this manner, speed of travel and slope data can be synchronized (in real-time) with digital video, and concurrently recorded slope time intervals can be made equally divisible with digital or analog video frame per second rates.

FIG. 4 shows the major elements of the preferred embodiment which are recorded on the media 20 in a timeline format. The video data 66 for the video files 52 and course data 68 for the table files 56 are collected simultaneously into a temporary database 70. The audio files 54 and the software program 18 (if to be included) are then added to complete the database 70 and the media 20 is written. The audio files 54 and the software program 18 may be added to the database 70 at any time relative to collecting the video data 66. This is the case even for environmental audio files 62, which may be captured in a real world setting (not necessarily the same as that for the video data 66), or which may be derived from "stock" data for natural sounds, which may not even have origins in true nature settings.

The software program 18 (FIG. 3) is used to perform the three conventional tasks of input, output and processing. It accepts as input the data files 50 from the media 20, and also speed sensor 24 (an optional other sensors) data from the M-S converter 14 as it arrives via the communications link 26. As output it plays back the video files 52 and the audio files 54 from the media 20 and it transmits control data through the communications link 26 to the M-S converter 14 for dynamic control of the resistance system 22, to correlate a user's performance on the exercise equipment 12 with the rate and manner in which contents of the media 20 are being played.

In the preferred embodiment, the software program 18 employs a model time based process where the software program 18 computes speed and position within the present exercise course at roughly 60 ms intervals. The M-S converter 14 feeds data to the software program 18 asynchronously. The terrain data corresponding to the current "position" in the exercise course is then fetched and processed and the process adjusts the video playback rate to synchronize the video position with the virtual position of the user within the exercise course. This model time based process is interrupted by the arrival of new speed data, and runs an extra cycle to re-compute speed and position when new speed data from the M-S converter 14 arrives. Therefore, in the preferred embodiment the M-S converter 14 transmits such speed data at a rate of up to once every 60 ms, with more frequent transmissions improving the smoothness of the computations, and the process directs setting the resistance system 22 each time such a reporting from the speed sensor 24 is received. The resistance level desired is computed as the time average of the power levels that the model time based process calculates between each speed report. In this manner the M-S converter 14 is able to controllably adjust the resistance system 22 on the exercise equipment 12 as a function of the speed data received and the parameters contained in course information (i.e., terrain characteristics; see e.g., FIGS. 7 and 8) which are stored on the media 20. However, the synchronization rate used for video playback is somewhat complicated by the fact that the video timing is variable and need not necessarily correlate with real time. The inventors have addressed this by transmitting control data for the resistance system 22 once for every second of video time, and by omitting any such control data for any corresponding video "seconds" which are skipped. In this manner the software program 18 maintains correct alignment between the video playback and the difficulty feedback the user experiences from the resistance system 22. Value added features such as terrain characteristic graphs and the user's relative course location can also easily be provided, in pop-up windows on a television 46 used as monitor 25 or on a separate computer monitor 48.

For the actual playback of the video files 52, conventional ActiveMovie filtergraphs are used in the preferred embodiment to produce the desired output characteristics. This provides considerable flexibility, permitting use of different "movie" formats and permitting the software program 18 to include extensive user command capabilities, like play, pause, resume, reset, and stop. Further, in the preferred embodiment, the software program 18 is used to influence exercise system 10 playback speed with a function using a denominator of 1,000 to convert the integer value speed data received into a floating point value to provide adjustment resolution and permit the user to have a considerable degree of control so that they may fine tune their exercise experience.

Many aspects of the software program 18 may be conventional. For example, widely used techniques for the for playback of video and audio data exist, including ones for varying the speed of such playback (e.g., the already noted ActiveMovie technology). Similarly known are techniques for storing data tables and controlling micro processor and communications circuitry (information for the later is typically provided by the respective manufacturers). Thus, while creation of the software program 18 is a major task, it is nonetheless one will within the capability of skilled programmers using present computer languages. The inventors presently use Visual C++ and the Microsoft Foundation Class library (both T/M of Microsoft) to write the 32 bit routines for communicating with the micro controller 28 used in the M-S converter 14, and they use ActiveMovie to play back video files 52 in AVI or MOV file formats. This also permits the software program 18 to run well under the widely used Windows95 and WindowsNT operating systems (both T/M of Microsoft).

In operation, the exercise system 10 is highly user interactive. However, the interactive features are not intrusive, as is the case for many prior art system. A setup procedure in the software program 18 provides instruction on the selection of exercise equipment 12 from a list of compatible types. Once a selection is made, the exercise system 10 then initializes itself to accept user speed data captured from the particular exercise equipment 12 chosen. The user is also asked to specify a desired nominal level of difficulty at which they would like to exercise (e.g., easy, realistic, hard), the type and parameters of audio output desired (e.g., volume, music or nature sounds, etc.), and what feedback information they would like to additionally see while exercising (e.g., pulse, speed, distance, calories, etc.). This information as feedback can be displayed on the monitor 42 (e.g., superimposed upon the video playback), on a display unit 72 (FIG. 2) incorporated into the exercise equipment 12, or even on another separate display device. Thus, a user may setup the exercise system 10 once for a particular exercise equipment 12, and then as needed for particular exercise sessions, and then not have to bother with anything further thereafter, because the exercise system 10 can take over.

Figure 5:
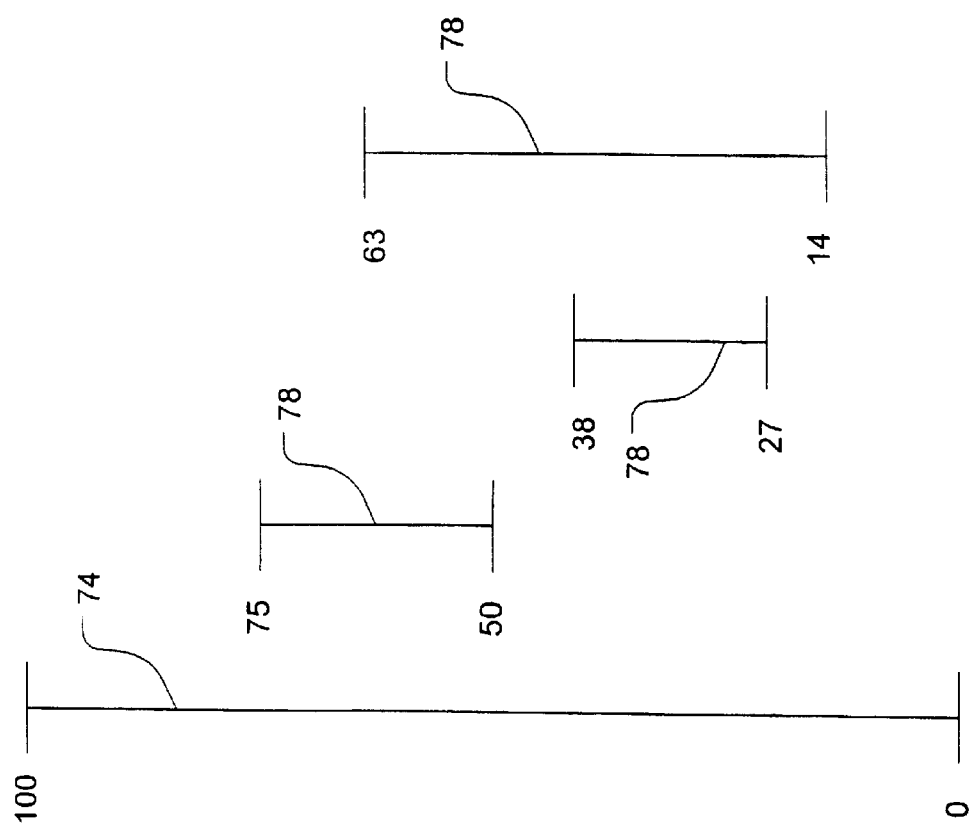
FIG. 5 is a graph illustrating relationships between the resistance range of the exercise system and typical course sequences, one where slope is a varying terrain characteristic.

FIG. 5 depicts how an interactive difficulty function in the preferred embodiment works. The possible range of resistance settings of the exercise equipment 12 is mapped to a linear integer equipment range 74 between 0 and 100. The range of terrain characteristics for a course is then normalized and mapped into this equipment range 74. For each course, the table files 56 (FIG. 3) in the media 20 are used to create a lookup table 76 (FIG. 7) of sub-ranges 78 which correlate normalized terrain characteristic values with the relative time that the characteristic value was collected. A simple multiplier is then used to determine the extent of the sub-range 78 of the normalized characteristic data within the full dynamic equipment range 74 of the exercise equipment 12. This multiplier is determined empirically by matching the resistance of the exercise equipment 12 to the resistance of the simulated in situ exercise. Calibration of actual terrain characteristics with settings of the particular resistance system 22 used is common to all media 20, although the range and time progression of characteristics of course vary depending upon the unique terrain represented within each course.

Figure 6:
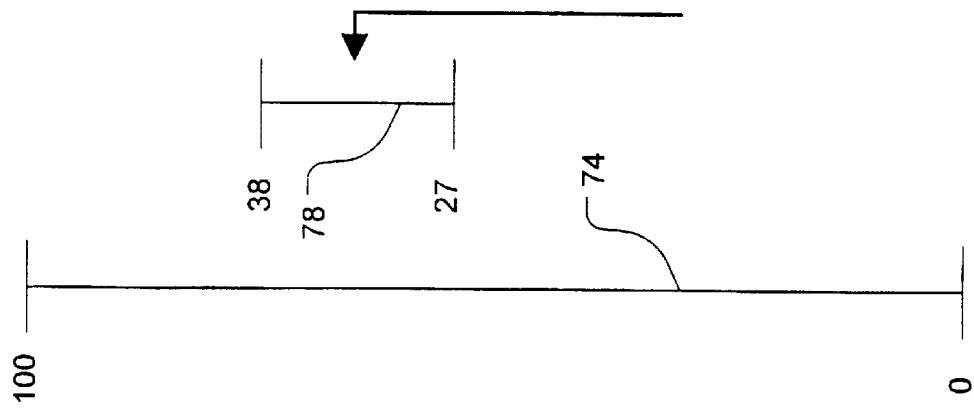
FIG. 6 is a graph illustrating the effect on one of the relationships of FIG. 5 when the user requests an increase in difficulty.

FIG. 6 depicts how the user has the ability at any time to shift the sub-range 78 of the terrain characteristic data by increasing or decreasing the resistance setting of the exercise equipment 12. The relative terrain characteristic values will remain the same resulting in a simple linear shift in the overall resistance experienced by the user. This allows every unit of media 20 to be as challenging or effortless as the user desires.

Figure 7:
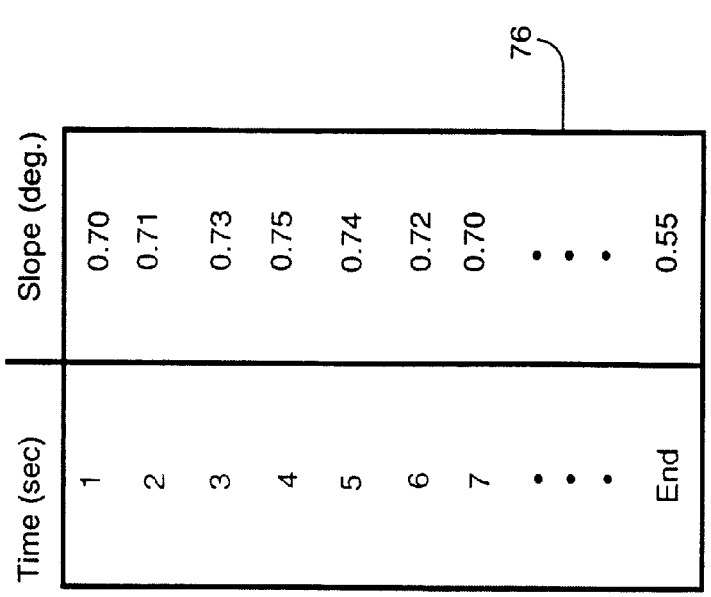
FIG. 7 is a representation of a typical lookup table which the exercise system could use during operation.
Figure 8:
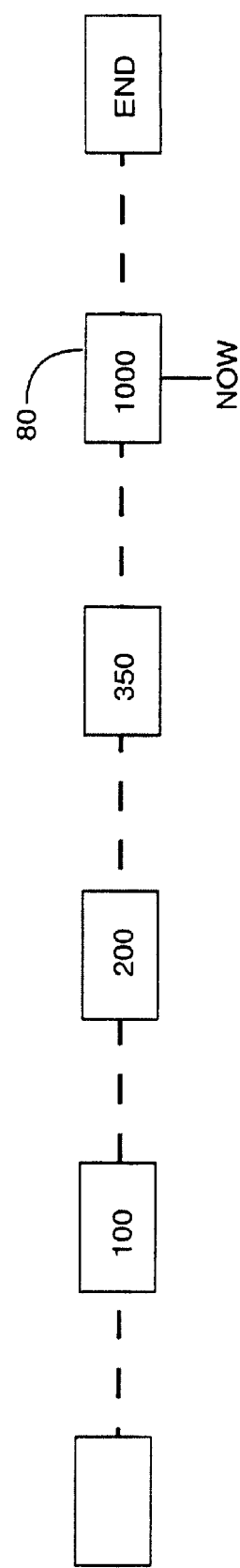
FIG. 8 is a representation of a typical linked list abstract data type which the exercise system could use during operation.

Terrain characteristic data is stored in the table files 56 on the media 20 (FIG. 3), along with the times at which they occur throughout the course (i.e., related to a position in the video file 52). Upon starting a course in the media 20, the table files 56 are loaded into temporary storage in the computer system 16. And the lookup table 76 is created. Terrain characteristic changes may then be loaded into a linked list 80 (as depicted in FIG. 8) or accessed directly from the lookup table 76 (FIG. 7). At specified time intervals the terrain characteristic data is accessed and the terrain characteristic information which corresponds with that time is loaded. In response to the terrain characteristic information, a resistance is calculated and transmitted to the M-S converter 14, which provides appropriate control for the resistance system 22 of the exercise equipment 12. In this manner, the terrain characteristic data representing the actual terrain of the real-world course being viewed is used to automatically further vary settings of the resistance system 22, thereby applying a dynamic difficulty level.

The video playback speed of the preferred embodiment is varied in response to user exertion (speed on the exercise equipment 12), under control of the software program 18, in response to incoming data from the speed sensor 24 for changes in speed. The video sub-system 40 ensures that video playback is smooth and consistent to minimize jerkiness. FIG. 8 depicts how the terrain characteristic data on the media 20 may be used by the software program 18 to indicate the video playback speed using a function VideoSpeed(Hwnd, Spd), where Spd is equal to 1,000, a base speed (i.e., a normal playback rate), and Hwnd is a pointer into the open video file 52. The video data 66, having previously been collected at typical speeds like 15 mph for biking, 6 mph for running, and 3 mph for hiking, thus permits a user traveling at the base speed to cause the VideoSpeed function to output 1,000 to the video player. The user then speeding up causes the number to go above 1,000, and slowing down has the reverse effect.

The various audio data stored in the media 20 are used in a number of different manners to enhance the video environment, to motivate the user to an optimum workout level, and to enhance the user's overall exercise experience. The voice audio files 58 will typically be played back at strategic points for the user's entertainment, distraction, and physiological encouragement. For example, they may be played when it is recognized that the user has traveled above or below an optimum workout level (e.g., to speed up, or to warn of high heart rate or other danger to the body, etc.). If desired, the music audio files 60 or the environmental audio files 62 may be played back constantly. For example, several small music audio files 60 may be stored on the media 20, each 1 to 2 minutes in length (about 20 to 30 kilobytes in size each), and played back either constantly or intermittently, and either individually, concatenated, or looped. In particular, music can be chosen to complement the portion of the workout in which a user is engaged, and it thus follows that different types of music can be played for warm-up, workout, and cool-down. Alternately, if desired, environmental audio files 62 may be played back in the same manners possible for the music audio files 60. In view of the particular ability of the exercise system 10 to simulate real-world exercise courses, it is anticipated that many users will prefer to listen to natural sounds which are consistent with a real world setting.

The comprehensive experience which the exercise system 10 provides makes high degrees of realistic simulation possible. On the right type of exercise equipment (e.g., an exercycle), features like cadence can be simulated. Simulated gravitational momentum is another particularly useful simulation feature. Changes in resistance can be controlled to simulate the effects of mass and momentum as would occur when traveling on the real slopes used to create terrain course data 68. Addition of a suitable heart rate sensor and appropriate modules in the software program 18 can provide the ability to have a constant metabolic rate workout (either as still further enhancement of the "gear" type simulation example below, or entirely separately).

Another simulation feature which the inventors have implemented is gear shifting. For example, a menu option of "constant level" may be provided in the software program 18, to simulate shiftable gears. This "shifting" can be directly user controlled or may be made automatic in relation to particular characteristics, like user speed (or complex variants of motion calculated from this) and terrain information (again in the table files 56 of course data 68). To implement this, the speed sensor 24 may be used to derive simulated ground distance traveled using a constant to convert revolutions (or fractional revolutions per unit time period) to distance traveled per unit time period. Since the speed sensor 24 is really only a cadence sensor or an RPM sensor, any number of virtual gears may be made available, say on an exercycle, and a different distance constant used in each case. This distance constant may be proportional to the virtual gear ratio. Then, proportionally to the virtual gear change, the resistance system 22 (i.e. braking) is also changed. For example, for a 21 gear system, 21 different distance constants would be used for each virtual gear. Likewise, different resistance factors would be used to change the brake resistance as an input to the M-S converter 14.

And another feature could be addition of a pacer. A pacer in the form of an animated object or a human figure (e.g., a cyclist or runner) can be included in the video data 66, by inclusion when initially capturing the video data 66, or by adding the pacer with conventional after-capture video editing techniques. Once its characteristics are initialized (say as part of the exercise session setup), and under control of the software program 18, the pacer can then appear in the video playback on the monitor 25 in positions relative to the user and commensurate with the user's efforts.

In addition to the above mentioned examples, various other modifications and alterations of the inventive exercise system 10 may be made without departing from the invention. Accordingly, the above disclosure is not to be considered as limiting and the appended claims are to be interpreted as encompassing the true spirit and the entire scope of the present invention.

INDUSTRIAL APPLICABILITY

The present exercise system 10 is well suited for application in a very wide range of settings. It may be used in traditional gyms and health clubs, in homes, in medical physical therapy facilities, and even in sports and military training. The invention by simulation can "bring" nature to its user, can "recreate" nature that may not presently exist, and can even bring users together in a "virtual" nature setting for exercise training, for communal exercise, or for competitive exercise or sports events.

By reintroducing nature into exercise, the exercise system 10 is a viable solution to the boredom of repetitive exercise in fitness and training regimens. Images and sounds of real-world environments can be stored on storage media and played back to provide users with the experience of a bike ride through the country, a hike in the mountains, or any of many other possible venues.

The exercise system 10 produces a realistic user-controlled environment promoting compliance with training and exercise regimes as well as self-efficacy in evaluating, prescribing, and planning a program of physical activity leading to better fitness. In unnatural settings like gyms, health clubs, homes, and medical facilities, users can immerse themselves in simulated natural settings produced by the exercise system 10, rather than be distracted by the reality of their actual surroundings.

The exercise system 10 can also recreate, virtually an unlimited number of times, a particular set of conditions for a particular exercise scenario. This permits users to realistically and effectively train, and to accurately benchmark their progress. Further, this can be done even when particular natural conditions are "out of season" or when actual natural settings are geographically too remote. For example, runner users might train for a foot race to the top of Mount Fuji, Japan. Many users in this example would be happy merely to exercise in such a simulated setting and to get into the physical shape required for such an event, while others would actually go on to compete in the annual summer footrace up Mount Fuji, secure in the knowledge that they had trained themselves in the most realistic possible manner (even more so than those living at the mountain could in some respects, since they would be limited by the weather changing seasonally). For another example, military users might train rowing of rafts for particular beach approaches, with simulated heavy currents, wind, and surf, but without the attendant risks of a real training exercise.

The exercise system 10 can also enhance or change the social content of exercise. For example, now bicyclists training for the Tour d'France race can "compete" with others similarly minded, or friends may take social rides through simulated creations of scenic Irish countryside. The exercise equipment 12 used for these examples need not even be in the same country. They may be part of a global implementation of the computer system 16 which is connected over a network like the Internet.

Of course, separated multiple users of the exercise system 10 in situations like those described above might want to communicate with and actively perceive each other. This is possible with realistic audio and even visual communication over networks in the computer system 16, using increasingly common technology (e.g., by incorporating "video conferencing" type capability into the exercise system 10). Further, for such inter-user audio-visual communication, when realistic user portrayal is optional or even unwanted, user substitutes can be employed. Techniques for this can be borrowed from the field of computer gaming, where avatars are the virtual-world counterparts of the real-world players. Thus the exercise system 10 could permit a fat person "wearing" a thin avatar or an old person wearing a young avatar to exercise with less self consciousness. Similarly, runners could train together "incognito," with only the individuals themselves actually knowing their respective genders and races.

The exercise system 10 could also be used for creating specific interactive exercises. In theory, a professional football running back can use suitable exercise equipment 12 to learn a new play. Using a 360-degree treadmill the running back could run a 40-second play in any one of 60 different ways. The needed amount of video data 66 could easily be held on one unit of media 20. As the running back makes choices in his running, the software program 18 would play the appropriate media 20 sequence corresponding to the user's actions.

The exercise system 10 may further be used to create particularly entertaining forms of exercise by combining it with other conventional technologies. For example, people who find exercise boring could be enticed into exercising in a manner which they enjoy and would return to by combining conventional video arcade game features with the exercise system 10.

The exercise system 10 is also useful to aid in rehabilitation. Adapting the exercise system 10 to exercise equipment 12 that is designed for handicapped or disabled individual's could aid in the individuals desire to continue physical therapy. Doctors involved in prescribing physical therapy could use the exercise system 10 to maintain motivation in their patients, even to the point that they would want to continue physical activity after their therapy ended. Elderly people could use the exercise system 10 with a strict cap on their heart rate, with the exercise equipment 12 instructed to automatically decrease the difficulty as needed. This would ensure a safe workout for any individual who is in need of exercise for rehabilitation.

The exercise system 10 is constructed using much conventional technology. Today some exercise equipment 12 already comes with a suitably controllable resistance system 22 and speed sensor 24. Further, in the computer system 16 and the M-S converter 14 the underlying hardware may be entirely convention, although combined in a unique manner for at least the M-S converter 14. Similarly, the media 20 may physically be entirely conventional, as may the hardware for recording it.

This exercise system 10 can also be implemented as a retrofit kit for exercise equipment 12 which either already has or may have added a speed sensor 24 and resistance system 22 capability. Such a retrofit kit could consist of a tap into an existing data link carrying speed and resistance information. Information from the exercise equipment 12 would be directed to the M-S converter 14, which would send the data to the computer system 16 via the communications link 26. The software program 18 would then send difficulty information back to the M-S converter 14, which would then suitably direct the resistance system 22 of the exercise equipment 12 in the various manners already discussed above. Even bike stands (i.e., not merely individual exercycles) with electromechanical braking devices could be retrofitted with the exercise system 10

A key point of consumer interest for the exercise system 10 is the variety possible in the media 20. Users of the invention could, via simulation, bicycle the Pacific Coast highway in California one day, and trek in the Pyrenees mountains of northern Spain the next. The media 20 of different course profiles could be distributed by video rental companies, transferred from a proprietary health club video server on a network, obtained via the Internet using an interactive television, or even transmitted using digital satellite.

For the above, and other, reasons, it is expected that the exercise system 10 of the present invention will have widespread industrial applicability. Therefore, it is expected that the commercial utility of the present invention will be extensive and long lasting.

What is claimed:

1. An interactive exercise system, comprising:

a computer system;

an exercise machine having resistance setting means for setting the resistance experienced by a user while exercising, and further having speed sensing means for sensing the speed at which said user exercises;

a controller suitable for controllably setting said resistance setting means, and further suitable for collecting speed data from said speed sensing means;

video playback means for playing from previously recorded storage media of video data including captured natural video image sequences; wherein said storage media further includes course data; and said computer system operates said video playback means and communicates with said controller and processes said speed data from said exercise machine and said course data from said storage media and calculates and appropriately directs said controller to control said resistance setting means of said exercise machine, thereby providing simulation of varying degrees of difficulty when said user operates said exercise machine, as would be consistent with what would be experienced traveling through a real exercise course.

2. The exercise system of claim 1, wherein:

said computer system includes audio playback means for playing previously recorded audio data; and said storage media further includes said audio data, thereby permitting presentation to said user of audio information as they exercise in the exercise system.

3. The exercise system of claim 2, wherein:

said audio data includes at least one member of the set comprising verbal audio data, environmental audio data, and music audio data; further wherein:

said verbal audio data communicates information to users of the exercise system;

said environmental audio data provides an illusion to users that exercise on the exercise system is occurring in a real exercise course nature setting; and said music audio data amuses, entertains, and sets an appropriate mood while users exercise with the exercise system.

4. The exercise system of claim 2, wherein said audio data is stored in at least one file storage format chosen from the set comprising WAV and MIDI formats.

5. The exercise system of claim 1, wherein:

said video data further includes at least one member of the set comprising textual video data and pictorial-instructional video data, further wherein:

said textual video data communicates written information to users of the exercise system; and said pictorial-instructional data communicates by informational demonstration to users of the exercise system.

6. The exercise system of claim 1, wherein said video data is stored in at least one file storage format chosen from the set comprising AVI and MOV formats.

7. The exercise system of claim 1, wherein:

said computer system and said controller are physically separated;

and the exercise system further comprises:

communications means for communicating said resistance data and said speed data between said controller and said computer system.

8. The exercise system of claim 7, wherein said communications means includes a cable.

9. The exercise system of claim 8, wherein:

said cable is a multi-pair telephone type terminated at both ends with connectors which are members of the set comprising RJ12 and RJ45;

said communications means further includes an adapter having a suitable plug for connecting to a computer port and a first socket suitable for accepting a first said connector at an end of said cable; and said controller includes a second socket suitable for accepting a second said connector at the other end of said cable.

10. The exercise system of claim 7, wherein said communications means includes a modulated infra-red light beam communications system.

11. The exercise system of claim 7, wherein said communications means includes an radio communications system.

12. A storage unit which is readable by a computer system able to dynamically control an exercise machine and a video playback means, the storage unit comprising:

a storage media unit;

course data including locational information and force information for points along a real exercise course stored on said storage media unit, thereby permitting the computer system reading an instance of the storage unit to dynamically control the exercise machine so that users experience a simulation of physical forces which would be encountered at specific locations along said real exercise course; and video data including captured natural video image sequences from said real exercise course stored on said storage media unit, thereby permitting the computer system to also control the video playback means so that said users experience a simulation of traveling through said real exercise course.

13. The storage unit of claim 12, further comprising audio data, to instruct and amuse said users of the exercise machine as they exercise.

14. The storage unit of claim 12, further comprising software for controlling the computer system.

15. The storage unit of claim 12, wherein storage media in at least one format chosen from the set comprising CD-R, CD-ROM, and DVD formats is used.

16. The storage unit of claim 12, wherein data is stored in at least one file format chosen from the set comprising WAV, MIDI, AVI, MOV formats.

17. A method of making a storage media which is readable by a computer system to dynamically control an exercise machine and operate a video playback means, the method comprising:

collecting locational information for points along a real exercise course;

collecting terrain characteristic information for said points;

creating course data by associating said locational information and said terrain characteristic information;

collecting video data including captured natural video image sequences; and storing said course data and said video data in a computer readable media unit, thereby permitting the computer system reading an instance of said media unit to dynamically control the exercise machine so that users experience a simulation of terrain characteristics which would be encountered along said real exercise course and further permitting the computer system to play said video data on the video playback means so that said users also experience a simulation of traveling through said real exercise course.

18. The method of claim 17, further comprising storing audio data in said media unit, to instruct and amuse said users of the exercise machine as they exercise.

19. The method of claim 17, further comprising storing software for controlling the computer system in said media unit.

20. The method of claim 17, wherein said step of collecting locational information includes referring to a position standard to determine positions of said points along said real exercise course, thereby permitting correlation of effective distances traveled by users of the exercise machine to geographic displacements of said points along said real exercise course.

21. The method of claim 20, wherein said position standard includes at least one member of the set comprising global position sensing systems, radio frequency triangulation systems, optical triangulation systems, altimeters, odometers, and inclinometers.

22. The method of claim 17, wherein said step of collecting force information includes measuring real forces present at said points along said real exercise course.

23. The method of claim 17, wherein said terrain characteristic information includes at least one member of the set comprising slope, altitude, temperature, wind speed, wind direction, current speed, current direction, and ground surface resilience.

* * * * *